United States Patent [19]

Burns

[11] Patent Number: 4,818,386

[45] Date of Patent: Apr. 4, 1989

[54] DEVICE FOR SEPARATING THE COMPONENTS OF A LIQUID SAMPLE HAVING HIGHER AND LOWER SPECIFIC GRAVITIES

[75] Inventor: James A. Burns, Elizabeth, N.J.

[73] Assignee: Becton, Dickinson and Company, Franklin Lakes, N.J.

[21] Appl. No.: 106,092

[22] Filed: Oct. 8, 1987

[51] Int. Cl.[4] .................. B01D 21/26; B01D 17/038
[52] U.S. Cl. ........................................ 210/97; 210/516
[58] Field of Search ................ 210/97, 515, 516, 518, 210/782, 789; 494/16; 422/101

[56] References Cited

U.S. PATENT DOCUMENTS

| | | | |
|---|---|---|---|
| 3,654,925 | 4/1972 | Holderith | 128/272 |
| 3,814,258 | 6/1974 | Ayres | 210/359 |
| 3,849,072 | 11/1974 | Ayres | 23/259 |
| 3,850,174 | 11/1974 | Ayres | 128/272 |
| 3,852,194 | 12/1974 | Zine | 494/16 |
| 3,862,042 | 1/1975 | Ayres | 210/516 |
| 3,882,021 | 5/1975 | Ayres | 210/136 |
| 3,887,464 | 6/1975 | Ayres | 210/117 |
| 3,887,466 | 6/1975 | Ayres | 210/131 |
| 3,890,237 | 6/1975 | Welch | 210/516 |
| 3,891,553 | 6/1975 | Ayres | 210/136 |
| 3,894,950 | 7/1975 | Ayres et al. | 210/131 |
| 3,894,951 | 7/1975 | Ayres | 210/136 |
| 3,894,952 | 7/1975 | Ayres | 210/136 |
| 3,897,337 | 7/1975 | Ayres | 210/136 |
| 3,897,340 | 7/1975 | Ayres | 210/314 |
| 3,897,343 | 7/1975 | Ayres | 210/516 |
| 3,901,219 | 8/1975 | Kay | 128/2 F |
| 3,909,419 | 9/1975 | Ayres | 210/518 |
| 3,919,085 | 11/1975 | Ayres | 210/516 |
| 3,920,549 | 11/1975 | Gigliello et al. | 210/516 |
| 3,920,557 | 11/1975 | Ayres | 210/516 |
| 3,929,646 | 12/1975 | Adler | 210/359 |
| 3,931,010 | 1/1976 | Ayres et al. | 210/109 |
| 3,931,018 | 1/1976 | North | 210/359 |
| 3,935,113 | 1/1976 | Ayres | 210/516 |
| 3,941,699 | 3/1976 | Ayres | 210/117 |
| 3,945,928 | 3/1976 | Ayres | 210/516 |
| 3,951,801 | 4/1976 | Ayres | 210/117 |
| 3,957,653 | 5/1976 | Blecher | 210/518 |
| 3,981,804 | 9/1976 | Gigliello | 210/516 |
| 3,986,962 | 10/1976 | Kessler | 210/516 |
| 4,027,660 | 6/1977 | Wardlaw et al. | 128/2 F |
| 4,055,501 | 10/1977 | Cornell | 210/516 |
| 4,057,499 | 11/1977 | Buono | 210/136 |
| 4,077,396 | 3/1978 | Wardlaw et al. | 128/2 F |
| 4,082,085 | 4/1978 | Wardlaw et al. | 128/2 G |
| 4,088,582 | 5/1978 | Murty et al. | 210/516 |
| 4,091,659 | 5/1978 | Massey, III et al. | 73/61.4 |
| 4,101,422 | 7/1978 | Lamont et al. | 210/516 |
| 4,147,628 | 4/1979 | Bennett et al. | 210/516 |
| 4,202,769 | 5/1980 | Greenspan | 210/516 |
| 4,243,534 | 1/1981 | Bulbenko | 210/656 |
| 4,417,981 | 11/1983 | Nugent | 210/209 |
| 4,569,764 | 2/1986 | Satchell | 210/511 |

Primary Examiner—Richard V. Fisher
Assistant Examiner—Linda S. Evans
Attorney, Agent, or Firm—Robert P. Grindle

[57] ABSTRACT

A device is provided for separating the components of a liquid sample by centrifugation by dividing that portion of the sample having a higher specific gravity from that portion having a lower specific gravity, by utilizing a dual component assembly arranged to move in an evacuated container into the area adjacent the two portions of the sample under centrifugal force. The assembly includes a substantially rigid core component which nests within a cup-shaped elastomeric component, and which components interact with each other to provide alternating dual seals and open flow paths in response to different pressure differentials on each side thereof.

11 Claims, 6 Drawing Sheets

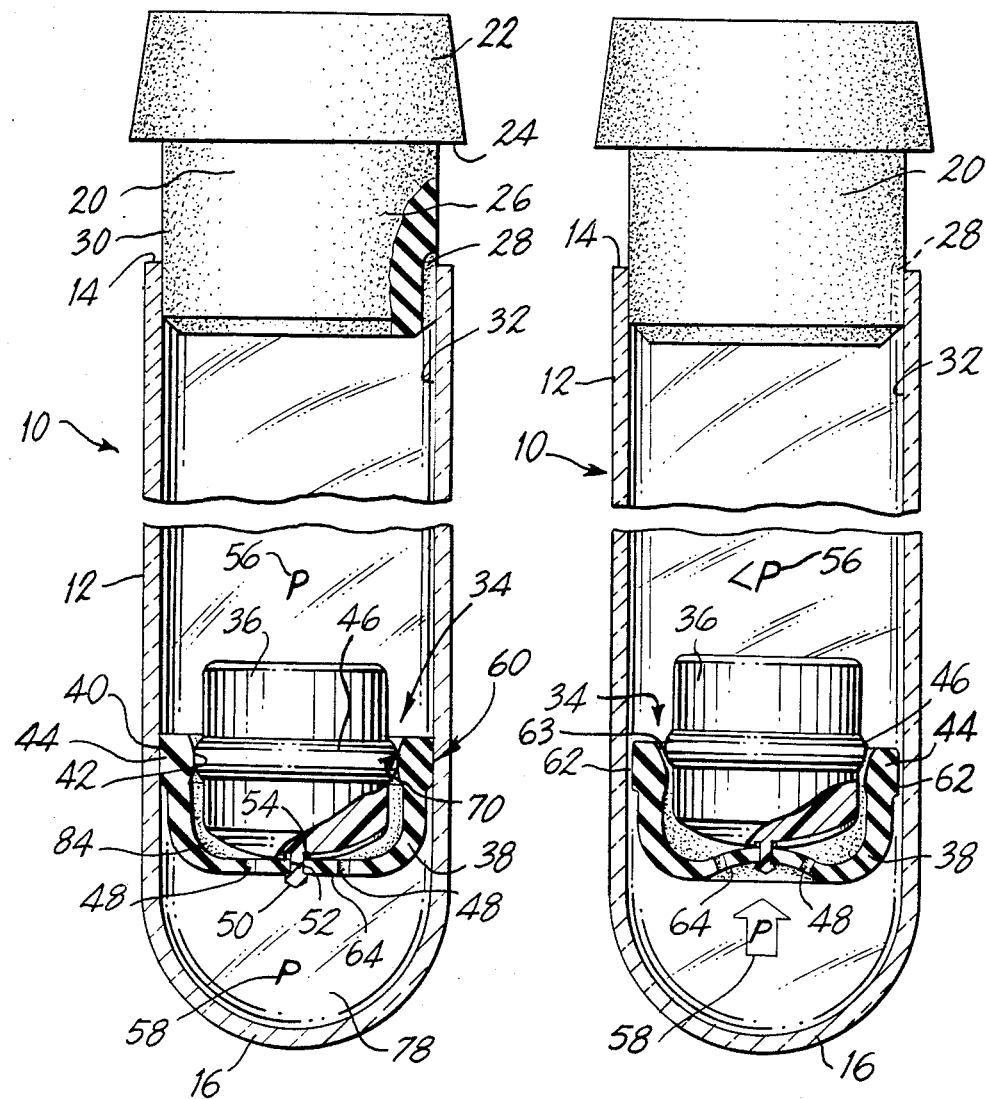

DEVICE FOR SEPARATING THE COMPONENTS OF A LIQUID SAMPLE HAVING HIGHER AND LOWER SPECIFIC GRAVITIES

BACKGROUND AND STATEMENT OF THE INVENTION

This invention relates generally to a device which separates what is usually called the heavier and lighter fractions of a liquid sample. More particularly, this invention relates to devices or assemblies utilizing an evacuated tube placed under centrifugation wherein a liquid sample is placed in the tube, and subsequently the tube is subjected to centrifugal force in order to cause the heavier fraction (or the fraction having the higher specific gravity) to the closed end of the tube while the lighter fraction (or that fraction having a lower specific gravity) moves toward the open end of the tube.

Such arrangements utilize some sort of barrier for moving into the area adjacent the two phases of the sample being separated in order to maintain the components separated for subsequent examination of the individual components. The thrust of all of the devices developed for use in the environment discussed above is to provide a barrier which divides cleanly the heavier and lighter fractions of the sample being separated.

When taking blood samples for test purposes, for example, whole blood generally is drawn into an evacuated collection tube, and the tube is centrifuged to separate the blood into the relatively lighter phase or component, as discussed above which is serum or plasma, and a heavier cellular phase. A variety of mechanical devices have been utilized in the past including piston-type arrangements for moving freely in the liquid sample in the evacuated tube so that the piston arrangements subsequently come to rest in the divided area between the heavier and lighter phases. While these mechanical arrangements have proved useful in a limited sense, they have not been entirely successful because they do not provide the clean separation discussed above.

The material utilized generally at this time for providing the barrier or separation between the heavier and lighter phases or the components having the lower and higher specific gravities include various thixotropic gel materials or sealants such as those described in U.S. Pat. No. 3,852,194, which is a mixture of silicone and hydrophobic silicon dioxide powders. Another form of thixotropic gel is a polyester gel which is presently utilized for a great many serum and/or plasma separation tube devices on the market. That material is taught and claimed in U.S. Pat. No. 4,101,422 issued July 18, 1978.

However, the present polyester gel serum separation tube requires, for example, special manufacturing equipment to prepare the gel and to fill the tubes. Both processes require rigid controls. Moreover, the shelf-life of the product is limited in that globules are sometimes released from the gel mass or network. These globules have a specific gravity that is less than the separated serum and will float in the serum and can clog the measuring instruments, subsequently, during the clinical examination of the sample collected in the tube.

Moreover, while the gel is chemically inert to blood samples, if certain drugs are present in the blood sample when it is taken, there can be an adverse chemical reaction with the gel interface.

With this invention, by contrast, a mechanical separator is utilized which is non-temperature dependent during storage and shipping, is more stable to radiation sterilization, and eliminates the need for a special transport tube which is required for gel separation devices as discussed above for improved barrier integrity during transportation. The arrangement herein utilizes a dual component mechanical assembly arranged to move in an evacuated tube under the action of centrifugal force in order to separate the two portions of the sample.

The assembly includes a substantially rigid core component which nests within a cup-shaped elastomer component. The solid component, under certain operating conditions, is movable within the cup-shaped component. The two components operate together, and complement each other under the differing pressure differentials which are inherent in serum separation tubes, to provide alternating dual seals and open flow paths in response to those pressure differentials. As such, the arrangement herein provides a much more precise division between the two portions being separated from the original sample introduced into the tube.

Before describing this invention in more detail, it should be well to note that the dual component device of the invention herein has a conventional specific gravity range within between about 1.03 and 1.09, and more specifically within the range of between about 1.05 and 1.06 so that the device will come to rest under centrifugal force substantially at the border between the heavier and lighter phases of the sample under consideration.

In addition, the central core portion of the dual component device may be comprised of a substantially rigid moldable thermoplastic material such as polyvinyl chloride, polystyrene, polyethylene, polypropylene, polyesters, and mixtures thereof, with a limitation being that the material is inert to the sample introduced in the assembly of the invention so as not to interfere with any desired subsequent testing. The cup-shaped portion, in turn, may be comprised of any natural or synthetic elastomer or mixtures thereof, with, again, the limitation concerning being inert to the sample of interest. The stopper may be comprised of similar elastomer combinations.

While the invention is directed to evacuated tubes in order to facilitate introduction of blood samples from the vein of a patient, it will be understood that the container in accordance with this invention does not necessarily need to be evacuated.

Other objects and advantages of this invention will be apparent from the following description, the accompanying drawings, and the appended claims.

DESCRIPTION OF THE DRAWINGS

FIGS. 1–8 are longitudinal sectional views illustrating the device of the invention, and showing the various components thereof in different positions of movement sequentially during the use of the device of the invention;

DETAILED DESCRIPTION OF THE INVENTION

Figures 3, 4:
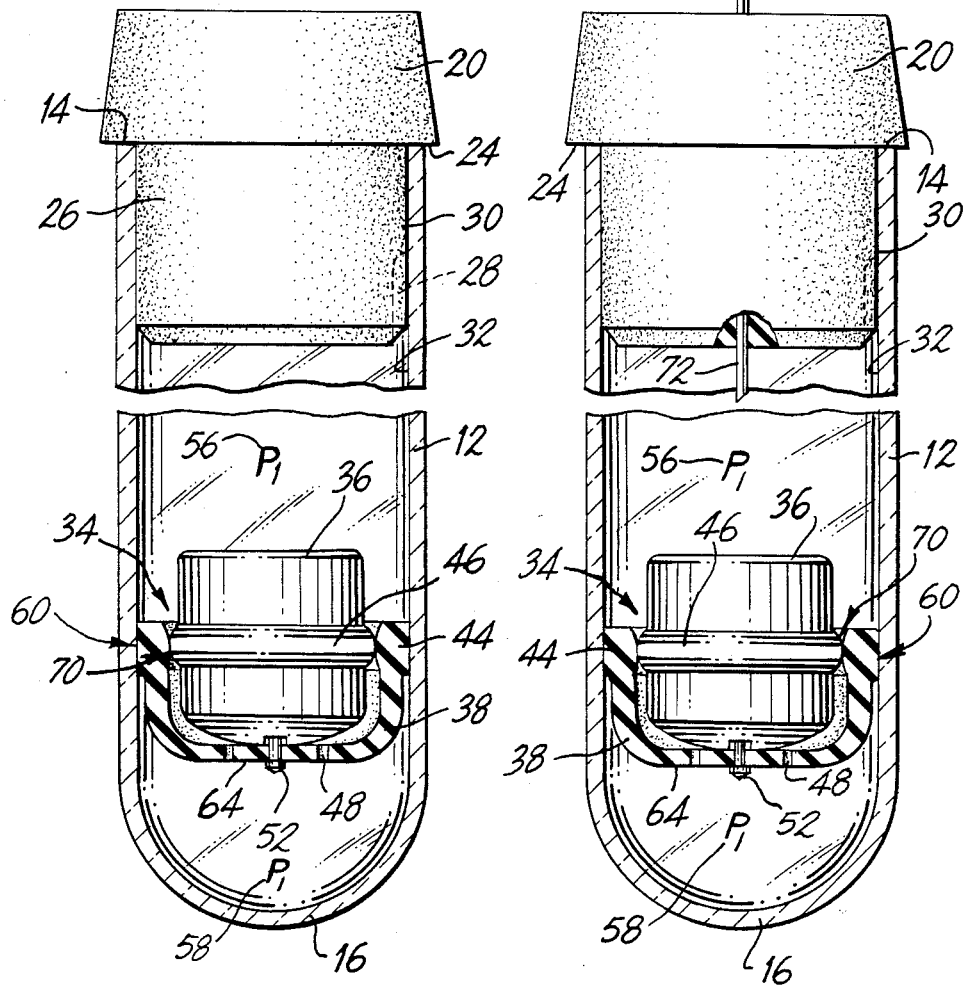

Referring to the drawings in which like reference characters refer to like parts throughout the several views thereof, FIG. 1 illustrates the invention in the form of a serum separation tube having a closed end and an open end with the latter being arranged to be sealed by a cooperating stopper so as to maintain a vacuum in the tube once the stopper is in place.

In FIG. 1, the assembly of the invention generally designated 10 includes tube 12 having an open end 14 and a closed end 16. Tube 12 is transparent so that the user may readily observe what is going on with the contents thereof. Tube 12 may be plastic but it is preferably glass.

Elastomeric stopper 20 is provided for insertion into the open end 14 of tube 12. Stopper 20 includes an upper annular portion 22 and a lower annular portion 26 of lesser diameter, with the lower portion 26 being arranged to be inserted into tube 12 so that the internal surface 32 of tube 12 adheres to and seals against the external surface 30 of annular portion 26. Because of the differing diameters of lower portion 26 and upper portion 22 of stopper 20, an annular ledge or abutment 24 is arranged to seat on the top surface of open end 14 of tube 12 to further enhance the sealing between tube 12 and stopper 20. Stopper 20 further includes a vent 28 positioned at one point in the circumferential extent of the lower portion 26 of stopper 20. The purpose of vent 28 will be described below. Tube 12 may be open at both ends (not shown) with a stopper 20 inserted in each end.

Further shown in FIG. 1 is a dual separator assembly 34, including a molded solid core 36 and an elastomeric cup-shaped flexible component 38. Solid core 36 nests in the cup-shaped elastomeric component 38. These two parts form dual seals 60 and 70. This is achieved by the annular ring portion 46 of solid core 36 cooperating with the upper annular ring portion 44 of the elastomeric cup-shaped lower portion 38.

Thus, surface 40 of portion 44 of the cup-shaped elastomeric portion 38 bears against the internal surface 32 of tube 12 under certain conditions of operation of the device herein, while internal surface 42 of portion 44 bears against the annular ring 46, as discussed above. These dual sealing positions come about when the pressure 56 above the dual component arrangement 34 is the same as the pressure 58 below the dual component 34.

Further as can be seen in FIG. 1, central core component 36 includes a snap connector 50, integral with central core component 36, which extends through a bore 52 in the bottom wall 64 of the elastomeric cup-shaped component 38. Groove 54 serves to provide liquid access adjacent the bottom of component 36. As can be seen in FIG. 1, the snap connector 50 extends through the bore and spreads to hold the two parts together. Further in bottom wall 64 of component 38 is a plurality of apertures 48 providing flow communication between area 78 below the dual separator assembly 34, and area 84 between the two components forming the dual assembly 34 in conjunction with groove 54.

In FIG. 1, because stopper 20 has not been seated within and sealed against the internal surface 32 of tube 12, the pressure differential between pressures 56 and 58 above and below dual assembly 34 are equal and at atmospheric pressure so that the dual assembly 34 provides the dual sealing action at annular contact points 60 and 70.

Referring now to FIG. 2, the positioning of the parts is shown for the assembly 10 when evacuation is initiated. In this connection, it should be borne in mind that it is within the purview of the practitioner-in-the-art to simultaneously seat the elastomeric stopper 20 in the tube 12 with the evacuation of the tube through vent 28.

That is, the application of a vacuum causes a withdrawal of air from the internal space of tube 12 simultaneously with the stopper gradually sliding into the tube into a sealing closure of the open end 14 of tube 12. Thus, in the position shown in FIG. 2, a pressure differential has developed between the pressure 56 above the assembly 34 ($<P$) and the pressure 58 below the assembly 34. As a result, the assembly 34 is unseated due to that pressure differential.

Referring to FIGS. 1 and 2, cylindrical core 36 is forced upward, and its outermost diameter is disengaged from the innermost diameter the cup-shaped portion 38. This causes a reduction in pressure, in addition, in a radial direction on the annular portion 44 of cup-shaped portion 38, along with the flexing upward of the bottom wall 64 which is in the form of a stretchable diaphragm. The outermost surface 40 of the upper annular sealing portion 44 of portion 38 moves radially inwardly from the inner surface 32 of tube 12. This causes a passage 62 and communication between the area above the assembly 34 and the area below assembly 34 as well as flow through passage 63 (former seal 70) between surfaces 42 and 46.

When the evacuation has been completed, as shown in FIG. 3, stopper 20 is completely inserted into the open end 14 of tube 12. In addition, because pressures 56 and 58 have again equalized ($P_1$), diaphragm wall 64 of the cup-shaped lower portion 38 of the assembly 34 moves downwardly into its normal position, and solid core 36 is pulled in a downward direction to return to the position causing the reestablishment of inner and outer dual seals 70 and 60.

Referring now to FIG. 4, a blood draw needle 72 has been inserted through a stopper 20 for introducing a blood sample into container 12 from the vein of a patient. At the initial start of a blood draw, the assembly 34 is in the normal position shown in FIG. 4 with equalized vacuum 56, 58 above and below the assembly 34, respectively.

Figures 5, 6:
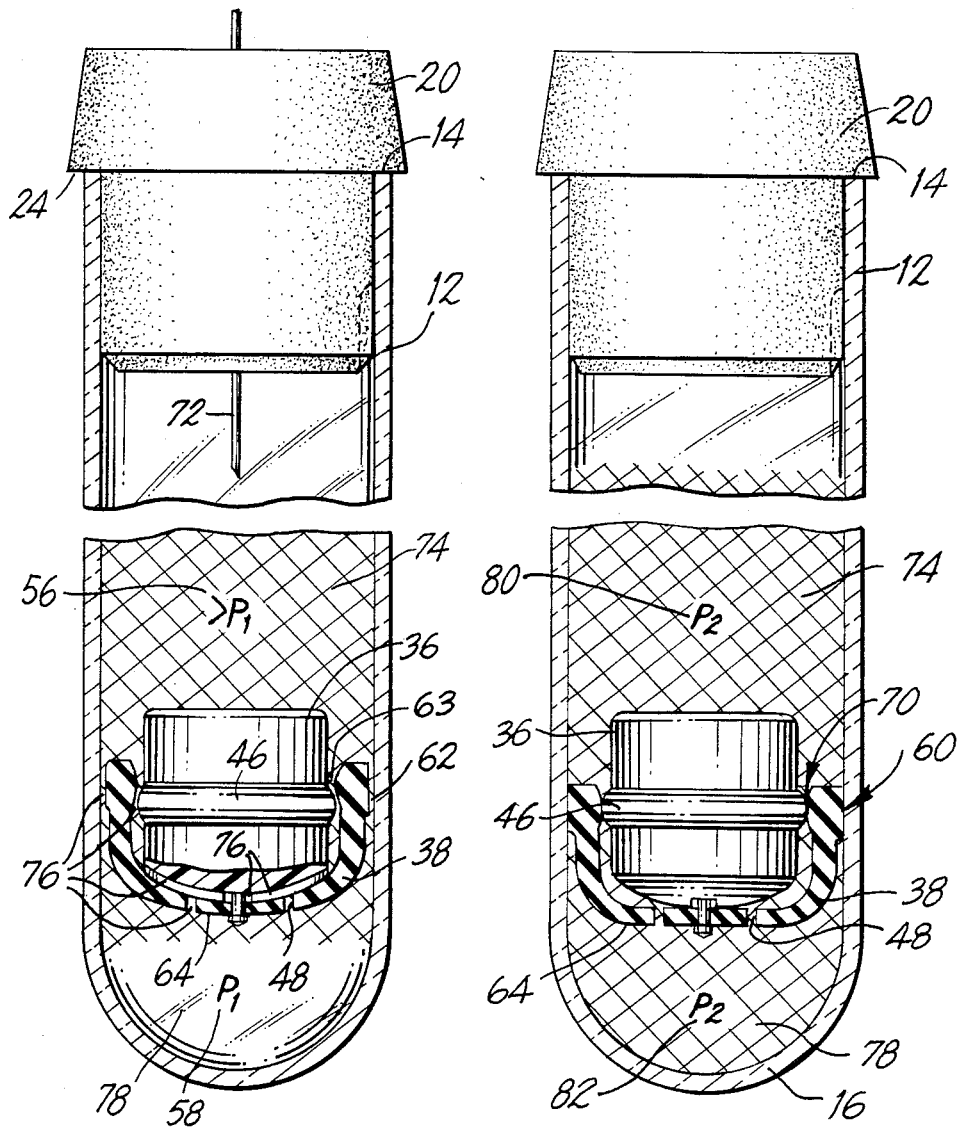

Referring now to FIG. 5, in this position, the blood draw continues and a pressure differential is set up again between the pressure 56 ($>P_1$) and the pressure 58 ($P_1$), with the pressure 56 being greater than the evacuated pressure established prior to blood draw. Because of the pressure differential, again, the separator assembly 34 moves into an unsealed position as shown in FIG. 5 with the solid core moving downwardly into the cup-shaped portion 38. Also, because of the pressure differential, the diaphragm bottom wall 64 of portion 38 moves downwardly.

As blood draw continues, blood passes through the various areas indicated at 76 in FIG. 5 from upper portion 74 above assembly 34 and into the bottom portion 78 below assembly 34. For this passage, of course, both dual seals 60 and 70 are opened for allowing the passage of blood. Once the quantity of blood required is introduced into container 12, the needle 72 is withdrawn and equalized pressure 80 ($P_2$) and 82 ($P_2$) is established above and below assembly 34 (FIG. 6). At this point, 64 has moved upwardly to its normal position resealing dual passages 60, 70.

Figures 7, 8:
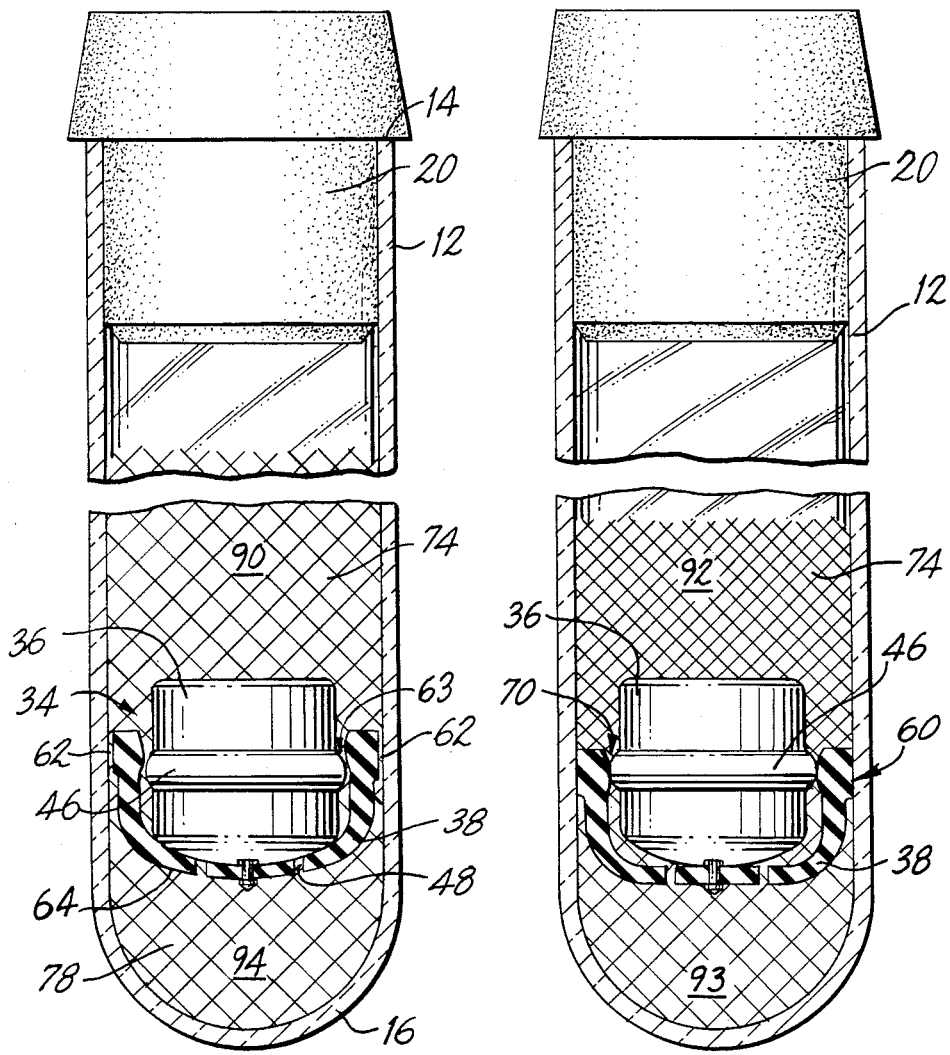

Then, the tube 12 is subjected to centrifugation. During centrifugation, the assembly 34 is forced into the unsealed position shown in FIG. 7. In this position, there is open passage between the area 78 below assembly 34 and the area 74 above assembly 34 establishing momentary equilibrium areas 90, 94 for the introduced sample just prior to separation. Moreover, because the assembly 34 has a specific gravity which is heavier than the serum and/or plasma or light phase of the sample being centrifuged in container 12, that portion of the sample having a specific gravity heavier than the assembly 34 moves below the assembly, while that portion of the sample which is lighter than the specific gravity of assembly 34 moves above the assembly. (FIG. 8) During centrifugation, the assembly 34 itself moves to the interface between the heavier phase 93 and the lighter phase 92 of the initial sample taken. At this point, when centrifugation ends, diaphragm 64 moves to the position shown in FIG. 8, and the dual seals 60, 70 move into place simultaneously with this movement of the assembly into its position at the interface, as discussed above. Because of this, a barrier is formed between the two phases.

Figure 9:
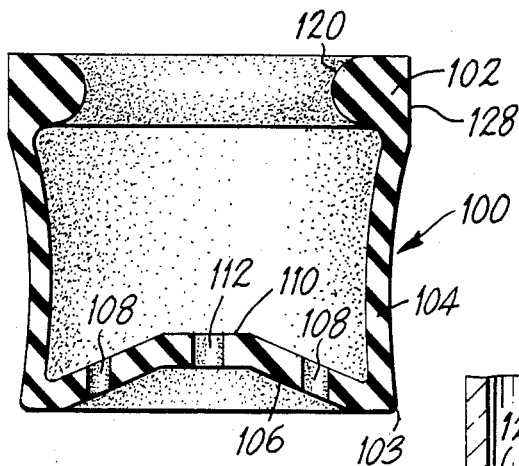
FIGS. 9–13 show a further embodiment illustrating the device of the invention, again showing the various components thereof and the positioning sequentially of those components in use.
Figure 10:
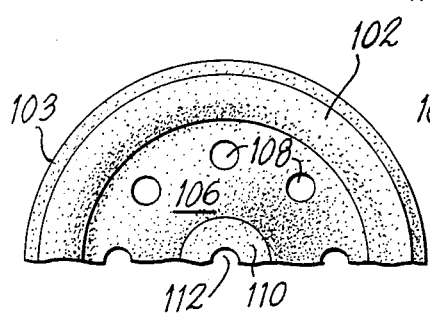
Figure 11:
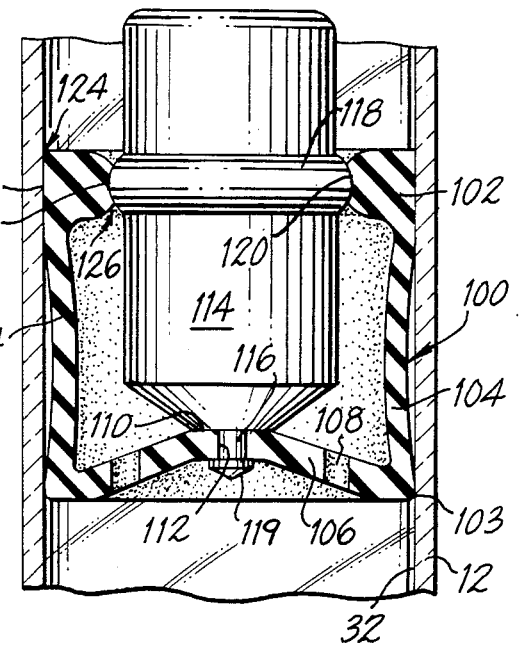

Referring now to FIGS. 9–13, inclusive, FIG. 9 shows a cross-sectional view of the cup-shaped component 100 of this embodiment. As can be seen, component 100 is configured somewhat differently than 38 in that side walls 104 are clearly thinner than bottom wall 106. Also, bottom wall 106 has a beveled configuration ending in a central plateau 110 which imparts more rigidity to wall 106. A plurality of liquid flow communication bores 108 are disposed around the circumference of wall 106, as clearly shown in FIG. 10. FIG. 10, in this regard is a top-plan view of component 100. Also, shown in FIGS. 9 and 11 is the upper annular sealing portion 102 of cup-shaped component 100 with inner 120 and outer 128 sealing surfaces.

FIG. 11 shows the solid central core component 114 with sealing ring 118 and sealing surface 122 cooperating in the sealing position with the resilient cup-shaped component 100. As can be seen in FIG. 11, an integral snap connector 116 depends from the bottom surface of core 114 with an enlarged portion 119 which snaps through bore 112 into locking engagement with the bottom surface of wall 106.

Thus, as can be seen in FIG. 11, the device is in the sealed position or mode as it is assembled and inserted into tube 12 and engaging surface 32 thereof. Side wall 104, as can be seen, has less curvature due to the compression of the outer seal 124 with surface 32. While the device is fairly tight at this period it can be moved or positioned in the tube. Bottom point i03 may touch surface 32 depending upon tolerances.

Figure 12:
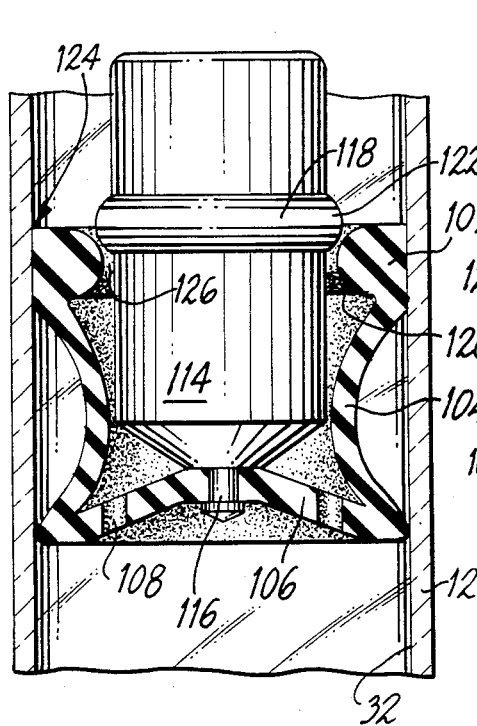

FIG. 12 shows the device in the unsealed upper position or mode which takes place during evacuation of tube 12. Due to the pressure differential above and below the dual component system, a force is applied upward on the system. The seal 124 resists most of the force imparted and the device remains generally stationary. The strength of the bottom wall 106 also resists this force. As can be seen, however, the thinner and weaker side wall 104 collapses until pressure equilibrium is reached, at which time the side wall will return to its natural state and pull core 114 back to its sealed position shown in FIG. 11 with dual seals 124 and 126.

Figure 13:
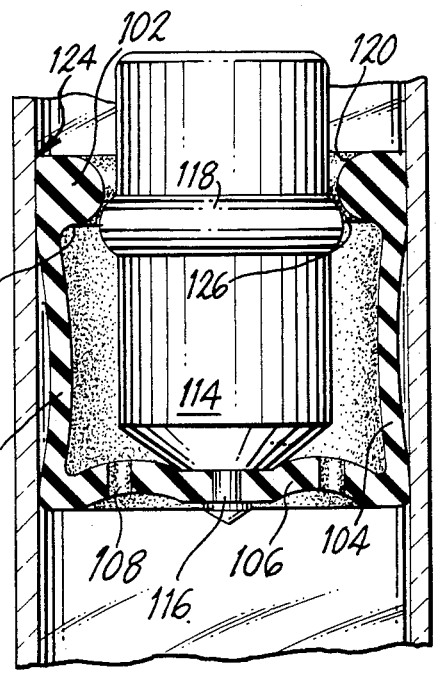

In FIG. 13, the device 100 is shown in the unsealed downward position or mode. This occurs during blood draw or centrifugation. During blood draw, the pressure differential creates a downward force. Thus, the beveled bottom wall 106 moves or collapses downward pulling core 114 into the unsealed position through snap connection 116, and then returns to normal when pressure equalizes. During centrifugation, the device moves up or down the tube in the unsealed position as described previously with the embodiment 34.

Thus, as can be seen from the above, the invention provides a dual assembly arrangement for separating a liquid sample into the components thereof having a higher specific gravity and the components thereof having a lower specific gravity, or more specifically the serum/plasma phase and the cellular phase of a blood sample. The arrangement herein utilizes a unique dual arrangement of a solid core with a flexible cup-shaped diaphragm portion holding the solid core, and with the two parts interacting with each other in response to variations in pressure differential on each side thereof to form dual seals at appropriate times during use, and to provide flow passage around this dual assembly, at appropriate times to cause the appropriate separation of the two phases.

Also, because the arrangement herein is a mechanical arrangement as opposed to a gel, less rigid control is required in order to prepare and manufacture the device of the invention. Moreover, less procedures are required in order to produce a product, in accordance herewith, having an extended shelf-life, with the product being chemically inert to any chemicals in a sample introduced into the device. In addition, the device of the invention is substantially more stable in the environment of radiation sterilization, and is not temperature dependent during storage.

While the form of apparatus herein described constitutes a preferred embodiment of the invention, it is to be understood that the invention is not limited to this precise form of apparatus, and that changes may be made therein without departing from the scope of the invention which is defined in the appended claims.

What is claimed is:

1. Apparatus for separating the constituents in a liquid sample introduced into said apparatus into constituents having a higher specific gravity from constituents having a lower specific gravity under the action of centrifugal force, comprising
   (a) a tube-shaped transparent container having a closed end and an open end and defining a sample receiving chamber;
   (b) a stopper for closing said open end of sad container; and
   (c) a dual barrier assembly movable axially in said container under the action of centrifugal force;
   (d) said dual barrier assembly having a specific gravity intermediate the specific gravity of constituents having a higher specific gravity and constituent having a lower specific gravity of a sample introduced into said container;
   (e) said dual barrier assembly providing selectively a dual annular seal and open passage therearound in response to pressure differentials in said container above and below said dual barrier assembly;
   (f) said dual barrier assembly comprising
      (1) a cup-shaped flexible portion;
      (2) said cup-shaped flexible portion having a first annular ring adjacent the upper edge thereof;
      (3) the outer circumferential edge of said first annular ring selectively movable into and out of sealing engagement with the internal wall of said container chamber in response to alternating equal and different pressures above and below said dual assembly;
      (4) means defining at least one opening in the bottom wall of said cup-shaped flexible portion providing flow communication therethrough;

(5) a round solid core portion nested in said cup-shaped portion;
(6) a second annular ring extending from the outer surface of said solid core portion;
(7) said solid core portion movable vertically in said cup-shaped portion for causing said first and second ring to move into and out of sealing engagement with each other in response to alternating equal and different pressures above and below said dual assembly; and
(8) means connecting said solid core portion and said bottom wall of said flexible cup-shaped portion.

2. The apparatus of claim 1, wherein
(a) said container is evacuated.

3. The apparatus of claim 2, wherein
(a) said stopper is comprised by an elastomer; and
(b) said stopper includes a vent extending axially along one point on the circumferential extent of the outer wall of said stopper for facilitating evacuation of said container.

4. The apparatus of claim 1, wherein
(a) said container is glass.

5. The apparatus of claim 1, wherein
(a) the specific gravity of said dual barrier assembly is within the range of between about 1.03 and 1.09.

6. The apparatus of claim 1, wherein
(a) said core portion is formed from a material selected from the group consisting of polyvinyl chloride, polyethylene, polypropylene, polystyrene, polyesters and mixtures thereof.

7. The apparatus of claim 1, wherein said cup-shaped portion is formed from material selected from the group consisting of natural elastomers, synthetic elastomers and mixtures thereof.

8. A dual barrier assembly for introduction into an evacuatable liquid collection tube, said assembly providing selectively, when inserted into an evacuatable liquid collection tube, a dual annular seal, and an open passage therearound in response to pressure differentials in a tube in which it is inserted, said assembly comprising
(a) a cup-shaped flexible portion;
(b) said cup-shaped flexible portion having a first annular ring adjacent the upper edge thereof;
(c) the outer circumferential edge of said first annular ring selectively movable into and out of sealing engagement with the internal wall of a tube chamber into which said assembly is inserted in response to alternating equal and different pressures above and below said dual assembly;
(d) means defining at least one opening in the bottom wall of said cup-shaped flexible portion providing flow communication therethrough;
(e) a round solid core portion nested in said cup-shaped portion;
(f) a second annular ring extending from the outer surface of said solid core portion;
(g) said solid core portion movable vertically in said cup-shaped portion for causing said first and second ring to move into and out of sealing engagement with each other in response to alternating equal and different pressures above and below said dual assembly; and
(h) means connecting said solid core portion and said bottom wall of said flexible cup-shaped portion.

9. The apparatus of claim 8, wherein
(a) the specific gravity of said dual barrier assembly is within the range of between about 1.03 and 1.09.

10. The apparatus of claim 8, wherein
(a) said core portion is formed from a material selected from the group consisting of polyvinyl chloride, polyethylene, polypropylene, polystyrene, polyesters and mixtures thereof.

11. The apparatus of claim 8, wherein said cup-shaped portion is formed from a material selected from the group consisting of natural elastomers, synthetic elastomers and mixtures thereof.

* * * * *